(12) United States Patent
Fukushima

(10) Patent No.: US 8,440,675 B2
(45) Date of Patent: May 14, 2013

(54) POTENTIATOR OF RADIATION THERAPY

(75) Inventor: Masakazu Fukushima, Tokushima (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/242,432

(22) Filed: Sep. 23, 2011

(65) Prior Publication Data

US 2012/0010165 A1  Jan. 12, 2012

Related U.S. Application Data

(63) Continuation of application No. 12/306,628, filed as application No. PCT/JP2007/000711 on Jun. 28, 2007.

(30) Foreign Application Priority Data

Jun. 30, 2006 (JP) .................................. 2006-181945

(51) Int. Cl.
*A01N 43/54* (2006.01)
*C07D 239/42* (2006.01)
*C07D 401/04* (2006.01)

(52) U.S. Cl.
USPC ......... 514/256; 442/78.36; 514/183; 514/247

(58) Field of Classification Search ...................... None
See application file for complete search history.

(56) References Cited

U.S. PATENT DOCUMENTS

| | | |
|---|---|---|
| 6,255,314 B1 | 7/2001 | Miyadera et al. |
| 6,294,535 B1 | 9/2001 | Yano et al. |

FOREIGN PATENT DOCUMENTS

| | | | |
|---|---|---|---|
| EP | 1 080 726 A1 | | 3/2001 |
| EP | 1080726 A1 | * | 7/2001 |
| WO | 96 30346 | | 10/1996 |
| WO | 98 13045 | | 4/1998 |

OTHER PUBLICATIONS

Nishimura Int. J. Clin. Oncol. (2004), vol. 9, pp. 414-420.*
Abraham Goldin, et al., "Search for New Radiation Potentiators", International Journal of Radiation Oncology Biology Physics, vol. 4, No. 1-2, Jan. 1, 1978, XP026837885, pp. 25-35.
Yasumasa Nishimura. "Rationale for chemoradiotherapy", International Journal of Clinical Oncology, vol. 9, No. 6, 2004, pp. 414-420.
Gilles Calias, et al., "Randomized Trial of Radiation Therapy Versus Concomitant Chemotherapy and Radiation Theraphy for Advanced-Stage Oropharynx Carcinoma", Journal of the National Cancer Institute, vol. 91, No. 24, Dec. 15, 1999, pp. 2081-2086.

Branislav Jeremic, et al., "Hyperfractionated Radiation Therapy With or Without Concurrent Low-Dose Daily Cisplatin in Locally Advanced Squamous Cell Carcinoma of the Head and Neck: A Prospective Randomized Trial", Journal of Clinical Oncology, vol. 18, No. 7, Apr. 2000, pp. 1458-1464.
M. Al-Sarraf, et al., "Progress Report of Combined Chemoradiotherapy Versus Radiotherapy Alone in Patients With Esophageal Cancer: An Intergroup Study", Journal of Clinical Oncology, vol. 15, No. 1, Jan. 1997, pp. 277-284.
C. G. Moertel, MD, et al., "Therapy of Locally Unresectable Pancreatic Carcinoma: A Randomized Comparison of High Dose (6000 Rads) Radiation Alone, Moderate Dose Radiation (4000 Rads + 5-Fluorouracil), and High Dose Radiation + 5-Fluorouracil", Cancer, vol. 48, Oct. 15, 1981, pp. 1705-1710.
William Sause, MD, et al., "Final Results of Phase III Trial in Regionally Advanced Unresectable Non-Small Cell Lung Cancer", Chest /117/2/ Feb. 2000, pp. 358-364.
K. M. Tveit, et al., "Randomized controlled trial of postoperative radiotherapy and short-term time-scheduled 5-fluorouracil against surgery alone in treatment of Dukes B and C rectal cancer", British Journal of Surgery, vol. 84, 1997, pp. 1130-1135.

\* cited by examiner

*Primary Examiner* — Patrick Lewis
(74) *Attorney, Agent, or Firm* — Oblon, Spivak, McClelland, Maier & Neustadt, L.L.P.

(57) ABSTRACT

To provide a radiation therapy potentiator, which, when employed in combination with cancer radiation therapy, can reduce radiation dose and can mitigate adverse effects.
The invention provides a radiation therapy potentiator containing, as an effective ingredient, a uracil derivative represented by formula (1) (wherein $R^1$ represents a halogen atom or a cyano group; and $R^2$ represents a 4- to 8-membered heterocyclic group having 1 to 3 nitrogen atoms and optionally having as a substituent a lower alkyl group, an imino group, a hydroxyl group, a hydroxymethyl group, a methanesulfonyloxy group, or an amino group; an amidinothio group in which a hydrogen atom attached to a nitrogen atom may be substituted by a lower alkyl group; a guanidino group in which a hydrogen atom attached to a nitrogen atom may be substituted by a lower alkyl group or a cyano group; a lower alkylamidino group; or a 1-pyrrolidinylmethyl group) or a pharmaceutically acceptable salt thereof.

(1)

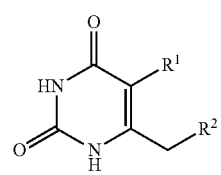

7 Claims, 1 Drawing Sheet

POTENTIATOR OF RADIATION THERAPY

CROSS-REFERENCE TO RELATED APPLICATIONS

This application is a continuation of U.S. Pat. No. 12/306,628 filed Dec. 24, 2008, now U.S. Pat. No. 8,148,381, which is a National Stage of PCT/JP07/00711 filed Jun. 28, 2007 and claims the benefit of JP 2006-181945 filed Jun. 30, 2006.

TECHNICAL FIELD

The present invention relates to a potentiator for radiation therapy (hereinafter referred to as radiation therapy potentiator), which, when employed in combination with cancer radiation therapy, can reduce the dose of radiation (hereinafter referred to as radiation dose) and can mitigate adverse effects.

BACKGROUND ART

Conventionally, cancer (malignant tumors) has been treated through surgical therapy, chemotherapy, immunotherapy, thermal therapy, and radiotherapy. In progressive stages III and IV, cancers such as stomach cancer, rectal cancer, pancreatic cancer, head and neck cancer, esophageal cancer, lung cancer, and breast cancer are usually treated through radiation therapy. Radiation therapy (currently total clinical radiation dose of 40 to 60 Gy) is difficult to employ singly for a long period of time, due to blood toxicity and adverse effects on the digestive system (e.g., thirst). Therefore, radiation therapy provides an insufficient clinical effect (anti-tumor effect). In recent years, in order to attain high anti-tumor effects, a combination of a chemotherapeutic agent and radiation (i.e., chemoradiotherapy) has become a standard treatment, and the combined treatment is thought to be successful in cancer treatment, as compared with the case of sole radiation therapy or sole chemotherapy (Non-Patent Document 1). For example, the following cases are disclosed: a combination of carboplatin/fluorouracil and radiation (Non-Patent Document 2) and a combination of cisplatin and radiation in the treatment of head and neck cancer (Non-Patent Document 3); a combination of fluorouracil/cisplatin and radiation in the treatment of esophageal cancer (Non-Patent Document 4); a combination of fluorouracil and radiation in the treatment of pancreatic cancer (Non-Patent Document 5); and a combination of cisplatin/vinblastine and radiation in the treatment of non-small-cell lung cancer (Non-Patent Document 6). In those cases, survival time is significantly prolonged as compared with sole radiation therapy. In the treatment of rectal cancer, patients who have been received chemoradiotherapy after surgery exhibit lower percent recurrence and have longer survival time, as compared with similar patients who have not received chemoradiotherapy (Non-Patent Document 7). However, currently, combined therapy of a chemotherapeutic agent and radiotherapy may cause adverse effects attributed to the chemotherapeutic agent itself, and in some cases medical treatment must be interrupted. In addition, mitigation of such adverse effects has not been fully attained.

Various attempts have been made to provide radiation sensitizers, which reduce radiation dose to thereby mitigate adverse effects without impairing radiation therapeutic effect. For example, certain nitroimidazole derivatives are known to serve as radiation sensitizers, and compounds such as misonidazole and etanidazole have been provided. However, such compounds have drawbacks; for example, excessively strong neurotoxicity when employed at a dose for attaining sensitization activity, and therefore cannot be used in practice. Meanwhile, in the treatment of a radiation-resistant tumor, a drug that potentiates radiation sensitivity is preferably used in combination. However, most of the reported radiation therapy potentiators (radiation sensitizers and similar agents) have neurotoxicity, which impedes development of radiation sensitizers.

[Non-Patent Document 1]
International Journal of Clinical Oncology, Vol. 9, No. 6 (2004): 414-490
[Non-Patent Document 2]
Calais et al., J. Natl. Cancer Inst. 91 (1999): 2081-2086
[Non-Patent Document 3]
Jeremic B. et al., J. Clin. Oncol. 18 (2000): 1458-1464
[Non-Patent Document 4]
Al-Sarraf M. et al., J. Clin, Oncol. 15 (1997): 277-284
[Non-Patent Document 5]
Moertel C. G. et al., Cancer 48 (1981): 1705-1710
[Non-Patent Document 6]
Sause W. et al., Chest 117 (2000): 358-364
[Non-Patent Document 7]
Tveit K. M. et al., Br. J. Cancer 84 (1997): 1130-1135

DISCLOSURE OF THE INVENTION

Problems to be Solved by the Invention

Thus, an object of the present invention is to provide a radiation therapy potentiator, which, when employed in combination with cancer radiation therapy, can reduce radiation dose and can mitigate adverse effects.

Means for Solving the Problems

In view of the foregoing, the present inventor has carried out extensive studies on uracil derivatives represented by formula (1) and pharmaceutically acceptable salts thereof in various aspects, and has found that combined use of such a compound and low-dose radiation results in potentiation of anti-tumor effect attributed to radiation and a therapeutic effect which is equivalent to or greater than that of a therapy solely employing high-dose radiation.

Accordingly, the present invention provides a radiation therapy potentiator containing, as an effective ingredient, a uracil derivative represented by formula (1):

[F1]

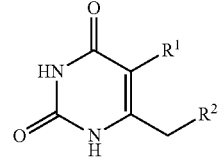

(1)

(wherein $R^1$ represents a halogen atom or a cyano group; and $R^2$ represents a 4- to 8-membered heterocyclic group having 1 to 3 nitrogen atoms and optionally having as a substituent a lower alkyl group, an imino group, a hydroxyl group, a hydroxymethyl group, a methanesulfonyloxy group, or an amino group; an amidinothio group in which a hydrogen atom attached to a nitrogen atom may be substituted by a lower alkyl group; a guanidino group in which a hydrogen atom attached to a nitrogen atom may be substituted by a lower alkyl group or a cyano group; a lower alkylamidino group; or a 1-pyrrolidinylmethyl group) or a pharmaceutically acceptable salt thereof.

The present invention also provides use of a uracil derivative represented by formula (1) or a pharmaceutically acceptable salt thereof for producing a radiation therapy potentiator.

The present invention also provides a method for potentiating radiation therapy, comprising administering, to a subject in need thereof, a uracil derivative represented by formula (1) or a pharmaceutically acceptable salt thereof.

The present invention also provides a method for treating cancer, comprising administering, to a subject in need thereof, a uracil derivative represented by formula (1) or a pharmaceutically acceptable salt thereof and performing cancer radiation therapy, in combination.

Effects of the Invention

Through employment of the radiation therapy potentiator of the present invention and radiotherapy in combination, an excellent cancer treatment effect can be attained by a lower radiation dose, and adverse effects can be mitigated. Therefore, a long-term, effective cancer treatment is realized.

Figure 1:
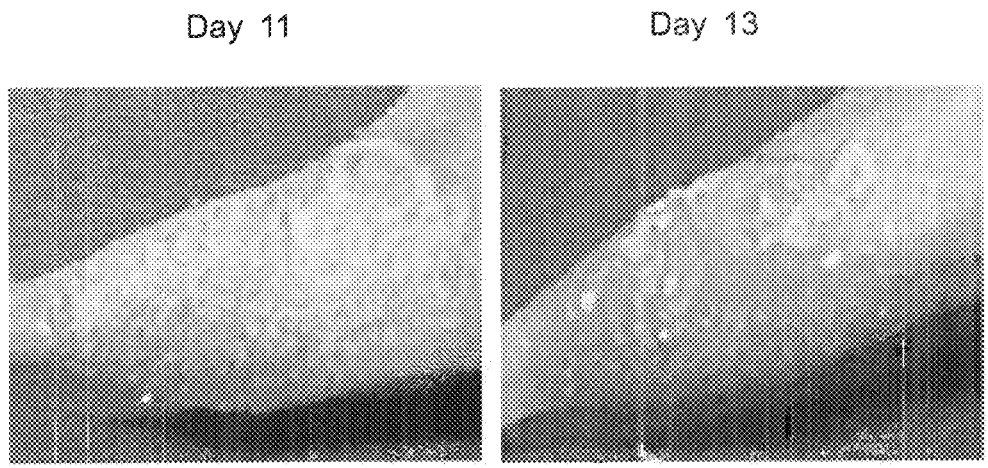
FIG. 1

Photographs showing skin conditions of a femoral region of a mouse belonging to a radiation-only group in Test Example 3 (days 11 and 13).

FIG. 2

Photographs showing skin conditions of a femoral region of a mouse belonging to a combination (radiation and administration of 5-chloro-6-[1-(2-iminopyrrolidinyl)methyl] uracil hydrochloride) group in Test Example 3 (days 11 and 13).

BEST MODES FOR CARRYING OUT THE INVENTION

Examples of the halogen atom ($R^1$) in formula (1) include fluorine, chlorine, bromine, and iodine, with chlorine and bromine being preferred.

Examples of the lower alkyl group which may serve as a substituent on the heterocyclic group, amidinothio group, guanidino group, or amidino group, represented by $R^2$, include linear-chain or branched-chain C1 to C4 alkyl groups. Specific examples include methyl, ethyl, n-propyl, i-propyl, n-butyl, i-butyl, sec-butyl, and t-butyl, with methyl being particularly preferred.

Examples of the 4- to 8-membered heterocyclic group ($R^2$) having 1 to 3 nitrogen atoms include 1-azetidinyl, 1-pyrrolidinyl, 2-pyrrolin-1-yl, 3-pyrrolin-1-yl, 1-pyrrolyl, 1-pyrazolidinyl, 2-pyrazolin-1-yl, 3-pyrazolin-1-yl, 4-pyrazolin-1-yl, 1-pyrazolyl, 1-imidazolidinyl, 2-imidazolin-1-yl, 3-imidazolin-1-yl, 4-imidazolin-1-yl, 1-imidazolyl, 1,2,3-triazol-1-yl, 1,2,4-triazol-1-yl, piperidino, 1-piperazyl, morpholino, 1-perhydroazepinyl, and 1-perhydroazocinyl. Among them, 1-azetidinyl, 1-pyrrolidinyl, 1-imidazolidinyl, and 1-imidazolyl are preferred, with 1-pyrrolidinyl being particularly preferred.

The heterocyclic ring may have, on the ring thereof, one or two substituents. Examples of such substituents include a lower alkyl, imino, hydroxyl, hydroxymethyl, methanesulfonyloxy, and amino. Specific examples of the heterocyclic group having an optional substituent include 1-azetidinyl, 1-pyrrolidinyl, 2,5-dimethylpyrrolidin-1-yl, 2-iminopyrrolidin-1-yl, 3-hydroxypyrrolidin-1-yl, 2-hydroxymethylpyrrolidin-1-yl, 3-methanesulfonyloxypyrrolidin-1-yl, 3-aminopyrrolidin-1-yl, 2-pyrrolin-1-yl, 3-pyrrolin-1-yl, 2-imino-3-pyrrolin-1-yl, 1-pyrrolyl, 1-pyrazolidinyl, 2-methylpyrazolidin-1-yl, 4-iminopyrazolidin-1-yl, 2-pyrazolin-1-yl, 3-pyrazolin-1-yl, 2-methyl-3-pyrazolin-1-yl, 5-imino-3-pyrazolin-1-yl, 4-pyrazolin-1-yl, 2-methyl-4-pyrazolin-1-yl, 3-imino-4-pyrazolin-1-yl, 1-pyrazolyl, 1-imidazolidinyl, 3-methylimidazolidin-1-yl, 2-iminoimidazolidin-1-yl, 2-imino-3-methylimidazolidin-1-yl, 2-imino-3-ethylimidazolidin-1-yl, 2-imino-3-isopropylimidazolidin-1-yl, 2-imidazolin-1-yl, 3-imidazolin-1-yl, 4-imidazolin-1-yl, 3-methyl-4-imidazolin-1-yl, 2-imino-4-imidazolin-1-yl, 2-imino-3-methyl-4-imidazolin-1-yl, 2-imino-3-ethyl-4-imidazolin-1-yl, 2-imino-3-isopropyl-4-imidazolin-1-yl, 1-imidazolyl, 2-methylimidazol-1-yl, 1,2,3-triazol-1-yl, 1,2,4-triazol-1-yl, piperidino, 1-piperazyl, 4-methylpiperazin-1-yl, morpholino, 1-perhydroazepinyl, and 1-perhydroazocinyl. Examples of preferred such heterocyclic groups include 1-azetidinyl, 1-pyrrolidinyl, 2-iminopyrrolidin-1-yl, 2-iminoimidazolidin-1-yl, 2-imino-3-methylimidazolidin-1-yl, 2-imino-3-ethylimidazolidin-1-yl, 2-imino-3-isopropylimidazolidin-1-yl, 2-imidazolin-1-yl, 2-imino-3-methyl-4-imidazolin-1-yl, 2-imino-3-ethyl-4-imidazolin-1-yl, and 1-imidazolyl.

Examples of the amidinothio group ($R^2$) in which a hydrogen atom attached to a nitrogen atom may be substituted by a lower alkyl group include an amidino group in which 1 to 3 hydrogen atoms of the three hydrogen atoms attached to the nitrogen atoms may be substituted by the aforementioned lower alkyl group. Among them, amidinothio, $N^1$-methylamidinothio, and $N^1,N^2$-dimethylamidinothio are particularly preferred.

Examples of the guanidino group in which a hydrogen atom attached to a nitrogen atom may be substituted by a lower alkyl group or a cyano group include a guanidino group in which 1 to 4 hydrogen atoms of the four hydrogen atoms may be substituted by the aforementioned lower alkyl group or cyano group. Among them, 1-guanidino, 1-methylguanidino, 3-methylguanidino, 2,3-dimethylguanidino, and 2-cyano-3-methylguanidino are particularly preferred.

The lower alkylamidino group is an amidino group to which one or two said lower alkyl groups are attached. Of these, methylamidino, ethylamidino, dimethylamidino, and diethylamidino are preferred.

Specific examples of preferred groups represented by $R^2$ include 1-azetidinyl, 1-pyrrolidinyl, 2-iminopyrrolidin-1-yl, 2-iminoimidazolidin-1-yl, 2-imino-3-methylimidazolidin-1-yl, 2-imino-3-ethylimidazolidin-1-yl, 2-imino-3-isopropylimidazolidin-1-yl, 2-imidazolin-1-yl, 2-imino-3-methyl-4-imidazolin-1-yl, 2-imino-3-ethyl-4-imidazolin-1-yl, 1-imidazolyl, amidinothio, $N^1$-methylamidinothio, $N^1,N^2$-dimethylamidinothio, 1-guanidino, 1-methylguanidino, 3-methylguanidino, 2,3-dimethylguanidino, methylamidino, and 1-pyrrolidinylmethyl. More preferred groups are 1-pyrrolidinyl, 2-iminopyrrolidin-1-yl, amidinothio, 3-methylguanidino, and 1-pyrrolidinylmethyl, with 2-iminopyrrolidin-1-yl being particularly preferred.

In preferred uracil derivatives represented by formula (1), $R^1$ is a chlorine atom, a bromine atom, or a cyano group; and $R^2$ is a 1-pyrrolidinyl group, a 2-iminopyrrolidin-1-yl group, an amidinothio group, a 3-methylguanidino group, or a 1-pyrrolidinylmethyl group.

No particular limitation is imposed on the uracil derivative (1) salt. However, preferred are acid addition salts and/or base salts which are produced through reaction with a pharmaceutically acceptable acid or basic compound. Examples of acid addition salts include salts with an inorganic acid such as hydrochloric acid, sulfuric acid, phosphoric acid, or hydrobromic acid; and salts with an organic acid such as oxalic acid, maleic acid, fumaric acid, malic acid, tartaric acid, citric acid, benzoic acid, acetic acid, p-toluenesulfonic acid, or methanesulfonic acid. Of these, hydrochloric acid salts and p-toluenesulfonic acid salts are preferred. Examples of base salts include salts with an alkali metal or an alkaline earth metal such as sodium, potassium, magnesium, or calcium; and salts with an amine such as ammonia, methylamine, dimethylamine, piperidine, cyclohexylamine, or triethylamine.

Specific examples of preferred uracil derivatives (1) or a pharmaceutically acceptable salt thereof include 5-chloro-6-(1-pyrrolidinylmethyl)uracil, 5-bromo-6-(1-pyrrolidinylmethyl)uracil, 5-cyano-6-(1-pyrrolidinylmethyl)uracil, 5-chloro-6-(1-azetidinylmethyl)uracil, 5-chloro-6-[1-(2-iminopyrrolidinyl)methyl]uracil hydrochloride, 5-bromo-6-[1-(2-iminopyrrolidinyl)methyl]uracil hydrochloride, 5-cyano-6-[1-(2-iminopyrrolidinyl)methyl]uracil, 5-chloro-6-[1-(2-iminoimidazolidinyl)methyl]uracil, 5-bromo-6-[1-(2-iminoimidazolidinyl)methyl]uracil, 5-chloro-6-(1-imidazolylmethyl)uracil hydrochloride, 5-chloro-6-(3-methylguanidino)methyluracil hydrochloride, 5-bromo-6-(3-methylguanidino)methyluracil hydrochloride, 5-cyano-6-(3-methylguanidino)methyluracil hydrochloride, 5-chloro-6-amidinothiomethyluracil hydrochloride, 5-bromo-6-amidinothiomethyluracil hydrochloride, 5-cyano-6-amidinothiomethyluracil hydrochloride, 5-chloro-6-(2-pyrrolidin-1-yl-ethyl)uracil, 5-bromo-6-(2-pyrrolidin-1-yl-ethyl)uracil, and 5-cyano-6-(2-pyrrolidin-1-yl-ethyl)uracil. Of these, 5-chloro-6-[1-(2-iminopyrrolidinyl)methyl]uracil hydrochloride, which is represented by the formula below, is particularly preferred.

[F2]

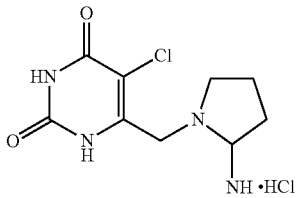

Compounds represented by formula (1) can be produced through, for example, a method disclosed in International Publication WO 96/30346 (pamphlet). The compounds of the present invention represented by formula (1), serving as an effective ingredient, are known compounds, and some pharmacological actions thereof are known. Specifically, there are known thymidine phosphorylase activity inhibitory action and anti-tumor effect potentiation action (International Publication WO 96/30346 (pamphlet)), cancer metastasis inhibitory action (International Publication WO 98/13045 (pamphlet)), action on mitigation of digestive tract disorders caused by an anti-tumor agent (International Publication WO 00/56337 (pamphlet)), and anti-HIV action (International Publication WO 01/34162 (pamphlet)). However, how the compounds function in radiation therapy has never been known.

Through employment of administration of the compound represented by formula (1) and radiation therapy in combination, cancer treatment effect provided by radiation can be remarkably potentiated, as compared with the case of sole radiation therapy. Thus, the compound represented by formula (1) is a useful radiation therapy potentiator. In addition, since the radiation therapy effect is potentiated, a sufficient cancer treatment effect can be attained by radiation at a lower dose. Thus, the compound represented by formula (1) also serves as a radiation dose-reducing agent in the treatment of cancer. Hitherto, when high-dose radiation therapy is continued, adverse effects such as blood toxicity, digestive tract toxicity, loss of appetite, boredom, and loss of body weight occur, to thereby impede long-term treatment in some cases. However, through employment of the compound represented by formula (1) and radiotherapy in combination, radiation dose can be reduced, and adverse effects can be mitigated. Therefore, radiation therapy can be performed for a longer period, whereby cancer treatment effect can be enhanced.

In addition to the uracil derivative represented by formula (1) or a pharmaceutically acceptable salt thereof (A), the radiation therapy potentiator of the present invention may further contain $\alpha,\alpha,\alpha$-trifluorothymidine (B).

The $\alpha,\alpha,\alpha$-trifluorothymidine (hereinafter may be abbreviated as FTD) is represented by formula (2). FTD is a nucleic acid derivative in which the methyl group of the 5-position of thymidine is substituted by a trifluoromethyl group and which was previously synthesized by Heidelberger et al. (J. Am. Chem. Soc., 84: 3597-3598, 1962; J. Med. Chem., 7: 1-5, 1964). An anti-tumor composition containing the compound represented by formula (1) and $\alpha,\alpha,\alpha$-trifluorothymidine is also known (International Publication WO 96/30346, pamphlet). However, how the composition functions in radiation therapy has never been known.

[F3]

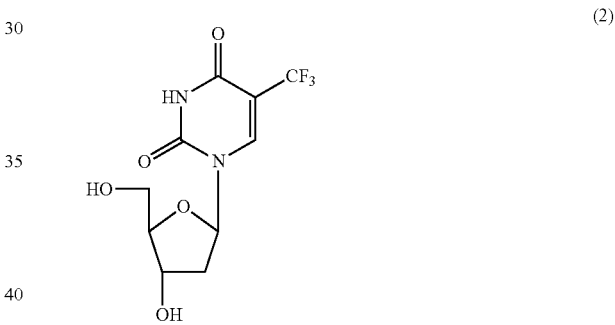

No particular limitation is imposed on the amounts of ingredients (A) and (B) contained in the potentiator, and ingredient (A) is preferably used in an amount of about 0.1 to about 500 mol with respect to 1 mol of ingredient (B), more preferably about 0.2 to about 10 mol, particularly preferably about 0.5 mol.

Among uracil derivatives serving as ingredient (A), preferred is 5-chloro-6-[1-(2-iminopyrrolidinyl)methyl]uracil or a pharmaceutically acceptable salt thereof.

Through employment of the composition containing ingredients (A) and (B) and radiation therapy in combination, cancer treatment effect provided by radiation can be remarkably potentiated, as compared with sole radiation therapy. Thus, the composition is a useful radiation therapy potentiator. In addition, since the radiation therapy effect is potentiated, a sufficient cancer treatment effect can be attained by radiation at a lower dose. Thus, the composition also serves as a radiation dose-reducing agent in the treatment of cancer. Hitherto, when high-dose radiation therapy is continued, adverse effects such as blood toxicity, digestive tract toxicity, loss of appetite, boredom, and loss of body weight occur, to thereby impede long-term treatment in some cases. However, through employment of the composition and radiotherapy, radiation dose can be reduced, and adverse effects can be mitigated. Therefore, radiation therapy can be performed for a longer period, whereby cancer treatment effect can be enhanced.

As used herein, the term "radiation therapy potentiator" refers to a drug that potentiates (enhances) radiation sensitivity (also called radiation sensitizer) through any action mechanism.

The radiotherapy intended in the present invention may be carried out through a protocol which is generally employed in this technical field and known to those skilled in the art. For example, the radiotherapy includes radiation of cesium, iridium, iodine, or cobalt. The radiotherapy may be systemic radiation (to acute leukemia, malignant lymphoma, and a certain type of solid cancer), but is preferably locally focused on site(s); i.e., tumor sites and solid cancer tissues (abdomen, lung, liver, lymph nodes, head, etc.). Typically, radiotherapy is carried out for 2 to 3 minutes a day and in a 25- to 30-divided manner (over about 5 to 6 weeks).

The radiation therapy potentiator of the present invention may be employed as an auxiliary agent with a main agent in radiotherapy of a malignant tumor which has intrinsically low radiation sensitivity or a malignant tumor which has acquired radiation resistance during radiation therapy. The radiation therapy potentiator of the present invention potentiates radiation sensitivity of tumor cells, whereby the radiation dose in the therapy can be reduced. Therefore, the treatment duration (exposure time) can be extended to a time longer than that predetermined by a generally employed protocol. In addition, adverse effects (e.g., stomatitis, myelopathy, radiation ulcer, and radiation pneumonia), attributed to radiation damage which inevitably occurs in radiotherapy, can be mitigated.

The radiation therapy potentiator of the present invention is administered in combination with radiation therapy, specifically before or after radiation therapy. In addition, the radiation therapy potentiator of the present invention, which potentiates radiation therapy effect as described above, may be employed in combination with other anti-tumor agents. Examples of such anti-tumor agents include platinum-containing drugs, taxane drugs, vinca alkaloid drugs, topoisomerase inhibitors, antimetabolites, and alkylating agents. More specific examples include one or more species of cisplatin, carboplatin, oxaliplatin, paclitaxel, docetaxel, vincristine, vinblastine, vinorelbine, vindesine, irinotecan hydrochloride, topotecan, etoposide, teniposide, doxorubicin, fluorouracil, tegafur, doxifluridine, capecitabine, gemcitabine, cytarabine, methotrexate, pemetrexed, cyclophosphamide, adriamycin, and mytomycin. When said other antitumor agents are employed in combination, age, sex, degree of symptom and adverse effects of patients, contraindication upon mixing, etc. are taken into consideration.

The radiation therapy potentiator of the present invention may be formed into generally employed pharmaceutical products with a pharmaceutically acceptable carrier; e.g., a filler, a bulking agent, a binder, a moisturizing agent, a disintegrant, a surfactant, a lubricant, or an excipient. When such a pharmaceutical product is administered to a mammal including a human, various pharmaceutical forms of administration may be selected in accordance with the purpose of the therapy. Specific examples include tablets, pills, powders, liquids, suspensions, emulsions, granules, capsules, suppositories, injections (liquids, suspensions, etc.), and ointments. Examples the carrier which may be employed for forming the tablets include excipients such as lactose, sucrose, sodium chloride, glucose, urea, starch, calcium carbonate, kaolin, crystalline cellulose, silicic acid; binders such as water, ethanol, propanol, simple syrup, glucose liquid, starch liquid, gelatin solution, carboxymethylcellulose, shellac, methylcellulose, potassium phosphate, and polyvinylpyrrolidone; disintegrants such as dry starch, sodium alginate, agar powder, laminaran powder, sodium hydrogencarbonate, calcium carbonate, polyoxyethylene sorbitan fatty acid esters, sodium lauryl sulfate, stearic acid monoglyceride, starch, and lactose; disintegration inhibitors such as sucrose, stearin, cacao butter, and hydrogenated oil; absorption promoters such as quaternary ammonium bases and sodium lauryl sulfate; moisturizing agents such as glycerin and starch; adsorbents such as starch, lactose, kaolin, bentonite, and colloidal silicic acid; and lubricants such as purified talc, stearic acid salts, boric acid powder, and polyethylene glycol. In accordance with needs, the tablets may further be modified to form coated tablets having a generally employed coating; e.g., sugar-coated tablets, gelatin-coated tablets, enteric tablets, film-coated tablets, double-layered tablets, and multi-layered tablets. In preparation of pills, there may be employed, for example, excipients such as glucose, lactose, starch, cacao butter, hydrogenated vegetable oil, kaolin, and talc; binders such as acacia powder, tragacanth powder, gelatin, and ethanol; and disintegrants such as laminaran powder and agar powder. Capsules may be prepared through a routine method; i.e., effective ingredients are mixed with the aforementioned carriers, and hard gelatin capsules or soft capsules are filled with the mixture. In preparation of suppositories, polyethylene glycol, cacao butter, higher alcohols, higher alcohol esters, gelatin, semi-synthesized glycerides, etc. may be used. In preparation of injection products, liquids, emulsions, and suspensions are preferably sterilized and isotonic to blood. For forming the injection products, a wide variety of known diluents may be used. Examples include water, ethyl alcohol, macrogol, propylene glycol, polyethoxylated isostearyl alcohol, and polyoxyethylene sorbitan fatty acid esters. In order to prepare isotonic solution, a sufficient amount of sodium chloride, glucose, or glycerin may be incorporated into such pharmaceutical products. Also, a generally employed solubilizing agent, buffer, analgesic agent, etc. may be incorporated into such pharmaceutical products. In preparation of ointments such as paste, cream, and gel, white petrolatum, paraffin, glycerin, cellulose derivatives, polyethylene glycol, silicone, bentonite, etc. may be employed as a diluent. Into the aforementioned pharmaceutical products, if required, a colorant, a preservative, a perfume, a flavoring agent, a sweetener, and other drugs may be incorporated.

No particular limitation is imposed on the amount of effective ingredient (A) or the total amount of effective ingredients (A) and (B) incorporated into the aforementioned pharmaceutical products, and the amount(s) may be appropriately selected from a wide range. Generally, the effective ingredient content of each pharmaceutical product is preferably 1 to 70 mass %.

No particular limitation is imposed on the administration route of the aforementioned pharmaceutical products, and the route is appropriately determined in accordance with the form of pharmaceutical products, the patient's age, sex, other conditions, severity of the disorder, and the like. The tablets, pills, powder, liquid, suspension, emulsion, granules, and capsules are perorally administered. The injection liquid or a mixture of the injection liquid and a generally employed replacement fluid such as glucose liquid or amino acid liquid are intravenously administered. The injection liquid is singly administered, intraarterially, intramuscularily, intradermally, subcutaneously, or intraperitoneally, in accordance with needs. The suppository is rectally administered. The ointment is applied to the skin, oral mucosa, etc. Among these administration routes, peroral administration is particularly preferred.

The dose of each effective ingredient of the pharmaceutical product of the present invention may be appropriately selected in accordance with the direction for use, the patient's age, sex, other conditions of a patient, severity of the disorder and the like. Generally, the dose of the uracil derivative (1) or a pharmaceutically acceptable salt thereof is about 0.01 to about 1,000 mg/kg/day, preferably about 0.5 to about 100 mg/kg/day. When α,α,α-trifluorothymidine is incorporated into the pharmaceutical product, the dose thereof is about 0.1 to about 100 mg/kg/day, preferably about 0.5 to about 50 mg/kg/day. Note that the pharmaceutical product of the present invention may be administered once a day or in a 2- to 4-divided manner.

Through employment of the radiation therapy potentiator of the present invention and radiotherapy in combination, an excellent cancer treatment method can be provided. No particular limitation is imposed on the tumor to which the treatment method can be applied. This method is particularly suitable for cancers with high radiation sensitivity. However, since the potentiator of the present invention can also increase radiation sensitivity of cancers that are considered to have low sensitivity, improvement of the effect of radiation therapy can be expected. Examples of the target cancer include head and neck cancer, esophageal cancer, stomach cancer, colon/rectal cancer, liver cancer, gallbladder/bile duct cancer, pancreatic cancer, lung cancer, breast cancer, bladder cancer, prostate cancer, cervical cancer, brain tumor, malignant lymphoma, acute leukemia, chronic leukemia, medulloblastoma, retinoblastoma, neuroblastoma, Wilms' tumor, Hodgkins' disease, multiple myeloma, plasmacytoma, thymoma, basal cell cancer, squamous cancer, Ewing's tumor, thyroid gland cancer, ovarian cancer, salivary gland cancer, teratoma, malignant melanoma, glioma, renal cell cancer, and osteosarcoma. Examples of preferred target cancers include head and neck cancer, esophageal cancer, stomach cancer, colon/rectal cancer, liver cancer, lung cancer, pancreatic cancer, and breast cancer. Examples of more preferred target cancers include head and neck cancer, esophageal cancer, liver cancer, lung cancer, pancreatic cancer, etc., which are difficult to treat through resection. Among them, lung cancer and head and neck cancer are particularly preferred.

EXAMPLES

The present invention will next be described more in detail by way of Test Examples, which should not be construed as limiting the invention thereto.

Test Example 1

(a) Preparation of Test Liquid

5-Chloro-6-[1-(2-iminopyrrolidinyl)methyl]uracil hydrochloride (hereinafter abbreviated as TPI) was suspended in a 0.5% (w/v) hydroxypropylmethyl cellulose (hereinafter abbreviated as HPMC) solution to adjust the concentration to 2.5 or 5.0 mg/mL, and the suspension was stirred at room temperature for about 10 minutes by means of a stirrer. Subsequently, the suspension was ultrasonicated under ice cooling for about five minutes, to thereby prepare a TPI drug liquid with a dose of 25 mg/kg/day or 50 mg/kg/day.

(b) Radiation (X-Ray) Irradiation Method

By means of a radiation apparatus (model: MBR-1505R2, product of Hitachi Medical Corp.), mice were irradiated with X-rays under such irradiation conditions that the unit dose to one mouse was adjusted to 2 Gy or 5 Gy, by controlling the distance from the radiation source to the mouse. Specifically, radiation was applied locally to the right femoral region of each mouse where cells of a human tumor strain had been transplanted. In order to avoid systemic irradiation, the mouse was placed in a lead box so that only the right leg was exposed to the radiation.

(c) Test Procedure

The human lung cancer strain (LC-11) subcutaneously transplanted into the back of a BALB/cA-nu mouse and grown beforehand were removed, cut into small pieces (about 2×2 mm$^2$) with scissors in physiological saline, and subcutaneously transplanted into the right femoral region of 5- to 6-week-old mice of the same strain with a transplantation needle. The thus-treated mice were bred for adaptation for at least 1 to 2 weeks and divided into a control group, radiation-only groups, a drug-only group, and radiation-drug combination groups, each group consisting of 6 mice, such that the average tumor volume and the standard deviation (S.D.) were equalized to a maximum extent between groups. Then, administration of the drug and irradiation were started. To each of the mice of the groups subjected to drug administration, the aforementioned TPI liquid was perorally administered, by means of an oral administration probe, once a day at a dose of 0.1 mL/10 g-body weight for 14 continuous days. The mice of the groups subjected to irradiation were irradiated with X-rays at a dose of 2 Gy or 5 Gy through the aforementioned method within about one hour after administration of the TPI liquid on the test day 1 and day 8. To the cancer-bearing mice of the control group (non-radiation/non-drug administration group) and those of the radiation-only groups, only 0.5% HPMC liquid was perorally administered through the same method for 14 continuous days.

The tumor volume of each mouse of the above groups, which was calculated by the equation 1 below, was determined before the start of the treatment test, and on day 3, day 5, day 8 (1 week after), day 11, day 15 (after termination of administration, 2 weeks after), day 18, day 21 (3 weeks after), day 25, and day 29 (4 weeks after). A relative tumor volume (RTV) to the tumor volume at the start of the test was obtained for each mouse. Table 1 shows the results along with the mean RTV and the standard deviation (S.D.) of each group. Then, the average tumor growth inhibition rate (IR: %) of each group with respect to the control group was calculated on day 15 and day 22 (after termination of the treatment period) on the basis of equation 2. The results are also shown in Table 1.

$$\text{Tumor volume(mm}^3\text{)=(long diameter)}\times\text{(short diameter)}^2\times 1/2 \quad \text{(Equation 1)}$$

$$\text{Tumor growth inhibition rate (IR,\%)=}[1-(\text{average tumor volume of a treatment group})/(\text{average tumor volume of the control group})]\times 100 \quad \text{(Equation 2)}$$

TABLE 1

| Group | Drug | Dose (mg/kg) | X-ray (Gy) | Day 15 RTV | Day 15 IR (%) | Day 22 RTV | Day 22 IR (%) |
|---|---|---|---|---|---|---|---|
| 1 | — | — | — | 6.5 ± 2.6 | — | 13.0 ± 4.6 | — |
| 2 | — | — | 2 | 3.9 ± 1.1 | 40.1 | 6.6 ± 1.9 | 49.1 |
| 3 | — | — | 5 | 2.8 ± 1.1 | 56.2 | 5.0 ± 1.7 | 61.3 |
| 4 | TPI | 50 | — | 6.6 ± 4.2 | -2.9 | 10.8 ± 5.8 | 16.7 |
| 5 | TPI | 25 | 2 | 2.5 ± 0.6 | 61.3 | 4.1 ± 0.9 | 68.7 |
| 6 | TPI | 50 | 2 | 2.4 ± 0.6 | 61.6 | 4.7 ± 1.3 | 64.1 |

(d) Test Results

Through X-ray radiation of 2 Gy, an anti-tumor effect was attained to the LC-11 tumor model on day 15 (40%) and on day 22 (49%). When TPI was administered at a dose of 50 mg/kg, virtually no anti-tumor effect was obtained. However, when administration of TPI at a dose of 25 mg/kg or 50 mg/kg and X-ray radiation of 2 Gy were employed in combination, the anti-tumor effect was 61.3% or 61.6% on day 15 and 68.7% or 64.1% on day 22, indicating that TPI significantly enhanced the anti-tumor effect of X-ray radiation of 2 Gy. These values are comparable to 56% and 61%, which were attained through sole X-ray radiation of 5 Gy. Thus, through combination with TPI, an X-ray radiation of a low dose can attain such a high anti-tumor effect as attained by an X-ray radiation of a high dose.

Test Example 2

(a) Preparation of Test Liquid (1)

TPI was suspended in a 0.5% (w/v) HPMC solution to adjust the concentration to 1.5 or 5.0 mg/mL, and the suspension was stirred at room temperature for about 10 minutes by means of a stirrer. Subsequently, the suspension was ultrasonicated under ice cooling for about five minutes, to thereby prepare a TPI drug liquid with a dose of 15 mg/kg/day or 50 mg/kg/day.

(b) Preparation of Test Liquid (2)

5-Chloro-6-aminouracil (hereinafter abbreviated as TUPI) was suspended in a 0.5% (w/v) HPMC solution to adjust the concentration to 5.0 mg/mL, and the suspension was stirred at room temperature for about 10 minutes by means of a stirrer. Subsequently, the suspension was ultrasonicated under ice cooling for about five minutes, to thereby prepare a TUPI drug liquid with a dose of 50 mg/kg/day.

(c) Radiation (X-Ray) Irradiation Method

By means of a radiation apparatus (model: MBR-1505R2, product of Hitachi Medical Corp.), mice were irradiated with X-rays under such irradiation conditions that the unit dose to one mouse was adjusted to 2 Gy or 5 Gy, by controlling the distance from the radiation source to the mouse. Specifically, radiation was applied locally to the right femoral region of each mouse where cells of a human tumor strain had been transplanted. In order to avoid systemic irradiation, the mouse was placed in a lead box so that only the right leg was exposed to the radiation.

(d) Test Procedure

The human lung cancer strain (LC-11) subcutaneously transplanted into the back of a BALB/cA-nu mouse and grown beforehand were removed, cut into small pieces (about 2×2 mm$^2$) with scissors in physiological saline, and subcutaneously transplanted into the right femoral region of 5- to 6-week-old mice of the same strain with a transplantation needle. The thus-treated mice were bred for adaptation for at least 1 to 2 weeks and divided into a control group, radiation-only groups, drug-only groups, and radiation-drug combination groups, each group consisting of 6 mice, such that the average tumor volume and the standard deviation (S.D.) were equalized to a maximum extent between groups. Then, administration of the drug and irradiation were started. To each of the mice of the groups subjected to drug administration, the aforementioned TPI liquid or TUPI liquid was perorally administered, by means of an oral administration probe, once a day at a dose of 0.1 mL/10 g-body weight for 14 continuous days. The mice of the groups subjected to radiation were irradiated with X-rays at a dose of 2 Gy or 5 Gy through the aforementioned method within about one hour after administration of the TPI liquid or the TUPI liquid on the test day 1 and day 8. To the cancer-bearing mice of the control group (non-radiation/non-drug administration group) and those of the radiation-only groups, only 0.5% HPMC liquid was perorally administered through the same method for 14 continuous days.

The tumor volume of each mouse of the above groups, which was calculated by the equation 1 in Test Example 1, was determined before the start of the treatment test, and on day 3, day 5, day 8 (1 week after), day 11, day 15 (after termination of administration, 2 weeks after), day 18, day 21 (3 weeks after), day 25, and day 29 (4 weeks after). A relative tumor volume (RTV) to the tumor volume at the start of the test was obtained for each mouse. Table 2 shows the results along with the average RTV and the standard deviation (S.D.) of each group. Then, the average tumor growth inhibition rate (IR: %) with respect to the control group was calculated on day 15, day 22, and day 29 (after termination of the treatment period) in a manner similar to that of Test Example 1. The results are also shown in Table 2.

TABLE 2

| Group | Drug | Dose (mg/kg) | X-ray (Gy) | Day 15 RTV | Day 15 IR (%) | Day 22 RTV | Day 22 IR (%) | Day 29 RTV | Day 29 IR (%) |
|---|---|---|---|---|---|---|---|---|---|
| 1 | — | — | — | 5.0 ± 1.5 | — | 8.9 ± 1.8 | — | 17.8 ± 3.8 | — |
| 2 | — | — | 2 | 3.1 ± 0.9 | 38.3 | 4.9 ± 1.8 | 45.4 | 9.7 ± 3.0 | 45.4 |
| 3 | — | — | 5 | 2.3 ± 0.7 | 54.9 | 3.3 ± 0.6 | 63.5 | 4.9 ± 1.0 | 72.6 |
| 4 | TUPI | 50 | — | 4.4 ± 1.8 | 12.7 | 7.4 ± 3.3 | 17.5 | 14.0 ± 6.3 | 21.4 |
| 5 | TUPI | 50 | 2 | 3.2 ± 0.8 | 36.6 | 5.3 ± 1.7 | 41.2 | 8.8 ± 2.5 | 50.2 |
| 6 | TPI | 50 | — | 4.7 ± 1.3 | 5.6 | 8.1 ± 2.0 | 9.8 | 14.5 ± 4.1 | 18.6 |
| 7 | TPI | 15 | 2 | 2.9 ± 0.8 | 42.1 | 4.2 ± 1.8 | 52.8 | 7.4 ± 3.2 | 58.4 |
| 8 | TPI | 50 | 2 | 2.5 ± 1.2 | 50.6 | 3.8 ± 2.1 | 56.9 | 5.4 ± 1.7 | 69.7 |

(e) Test Results

Through sole X-ray radiation of 2 Gy, an anti-tumor effect was attained to the LC-11 tumor model on day 15 (38%), on day 22 (45%), and on day 29 (45%). When the dose was 5 Gy, IRs were 55%, 63.5%, and 72.6%, respectively. When TUPI was singly administered at a dose of 50 mg/kg, virtually no anti-tumor effect was attained to the tumor model. Even when the administration of TUPI was combined with an X-ray radiation of 2 Gy, no potentiation of anti-tumor effect was observed. In contrast, when TPI was administered singly, virtually no anti-tumor effect was obtained. However, when administration of TPI at a dose of 50 mg/kg and X-ray radiation of 2 Gy were employed in combination, the anti-tumor effect was enhanced in response to the dose. Specifically, IRs of 50.6% on day 15, 57% on day 22, and 70% on day 29 were obtained. These values are comparable to those attained through sole X-ray radiation of 5 Gy.

Test Example 3

(a) Preparation of Test Liquid

TPI was suspended in a 0.5% (w/v) HPMC solution to adjust the concentration to 10.0 mg/mL, and the suspension was stirred at room temperature for about 10 minutes by means of a stirrer. Subsequently, the suspension was ultrasonicated under ice cooling for about five minutes, to thereby prepare a TPI drug liquid with a dose of 100 mg/kg/day.

(b) Radiation (X-Ray) Irradiation Method

By means of a radiation apparatus (model: MBR-1505R2, product of Hitachi Medical Corp.), mice were irradiated with X-rays under such irradiation conditions that the unit dose to one mouse was adjusted to 20 Gy, by controlling the distance from the radiation source to the mouse. Specifically, radiation was applied locally to the right femoral region of each mouse. In order to avoid systemic irradiation, the mouse was placed in a lead box so that only the right leg was exposed to the radiation.

(c) Test Procedure

BALB/cA-nu mice of 6- to 8-week-old were divided into a control group, a radiation-only group, and a radiation-drug combination group, each group consisting of 6 mice. Then, administration of the drug and irradiation were started. Since the drug (TPI) per se does not exhibit anti-tumor effect or adverse effects when continuously and orally administered, a drug-only group was not tested. The mice of the groups subjected to radiation were irradiated with X-rays of 10 Gy on day 1, day 2, and day 3 of the test. The mice of the radiation-drug combination group were similarly irradiated for three days, and the TPI liquid was perorally administered, by means of an oral administration probe, to each mouse once a day at a dose of 0.1 mL/10 g-body weight for 7 continuous days. The mice of the combination group were irradiated with X-rays at a dose of 10 Gy within about one hour after administration of the TPI liquid. To the normal mice of the control group (non-radiation/non-drug administration group), only 0.5% HPMC liquid was perorally administered through the same method for 7 continuous days.

(d) Evaluation of Degree of Skin Damage

After day 7 of the test, the degree of skin damage of the femoral region of each mouse, which was caused by radiation, was evaluated through a method of Douglas et al. (Douglas B. G., et al.: The effect of multiple small doses of X-rays on skin reactions in the mice and a basic interpretation. Radiation Res., 66: 401-426, 1976).

(e) Test Results

Figure 2:
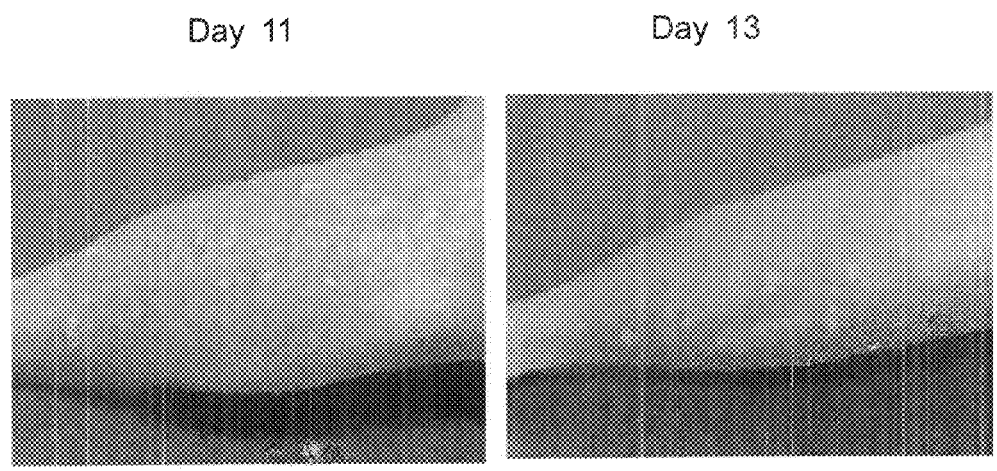

In the radiation-only group, all six mice exhibited moisture loss and keratinization of the skin (grade 1.0 to 1.5) and peeling of the skin surface (grade 2.5 to 3.0) from day 10, and these symptom were aggravated to the maximum extent on day 13 (FIG. 1). In contrast, in the radiation-drug (TPI) combination group, severe conditions were not observed, although slight damage (flare, swelling, or keratinization of the skin surface) was observed (FIG. 2). The mice of the control group exhibited no skin damage.

As a result, TPI was found to potentiate anti-tumor effect provided by radiation, but not to enhance radiation damage to the normal tissue (normal skin in the above test). Moreover, TPI was found to mitigate such radiation damage.

Test Example 4

(a) Preparation of Test Liquid I

α,α,α-Trifluorothymidine (hereinafter abbreviated as FTD) and TPI were suspended in a 0.5% (w/v) HPMC solution to adjust their concentrations to 5.0 mg/mL and 2.65 mg/mL, respectively, and the suspension was stirred at room temperature for about 10 minutes. Subsequently, the suspension was ultrasonicated under ice cooling, to thereby prepare a drug liquid with a dose of 50 mg/kg/day (as reduced to FTD). Hereinafter, the drug liquid is referred to as TAS-102.

The dose of the TAS-102 liquid is a "no observed adverse effect level" when the liquid is perorally administered to a mouse for 14 days.

(b) Preparation of Test Liquid II

FTD was suspended in a 0.5% (w/v) HPMC solution to adjust their concentrations to 5.0 mg/mL, and the suspension was stirred at room temperature for about 10 minutes. Subsequently, the suspension was ultrasonicated under ice cooling, to thereby prepare a FTD drug liquid with a dose of 50 mg/kg/day. The dose of FTD is a "no observed adverse effect level" when the liquid is perorally administered to a mouse for 14 days.

(c) Radiation (X-Ray) Irradiation Method

By means of a radiation apparatus (model: MBR-1505R2, product of Hitachi Medical Corp.), mice were irradiated with X-rays under such irradiation conditions that the unit dose to one mouse was adjusted to 2 Gy or 5 Gy, by controlling the distance from the radiation source to the mouse. Specifically, radiation was applied locally to the right femoral region of each mouse where cells of a human tumor strain had been transplanted. In order to avoid systemic irradiation, the mouse was placed in a lead box so that only the right leg was exposed to the radiation.

(d) Test Procedure

The human lung cancer strain (LC-11) subcutaneously transplanted into the back of a BALB/cA-nu mouse and grown beforehand were removed, cut into small pieces (about 2×2 mm$^2$) with scissors in physiological saline, and subcutaneously transplanted into the right femoral region of 5- to 6-week-old mice of the same strain with a transplantation needle. The thus-treated mice were bred for adaptation for at least 1 to 2 weeks and divided into a control group, radiation-only groups, drug-only groups, and radiation-drug combination groups, each group consisting of 6 mice, such that the average tumor volume and the standard deviation (S.D.) were equalized to a maximum extent between groups. Then, administration of the drug and irradiation were started. To each of the mice of the groups subjected to drug administration, the aforementioned TAS-102 liquid or FTD liquid was perorally administered, by means of an oral administration probe, once a day at a dose of 0.1 mL/10 g-body weight for 14 continuous days. The mice of the groups subjected to radiation were irradiated with X-rays at a dose of 2 Gy or 5 Gy through the aforementioned method within about one hour after administration of the TAS-102 liquid or FTD liquid on the test day 1 and day 8. To the cancer-bearing mice of the control group (non-radiation/non-drug administration group) and those of the radiation-only groups, only 0.5% HPMC liquid was perorally administered through the same method for 14 continuous days.

The tumor volume of each mouse of the above groups, which was calculated by the equation 1 in Test Example 1, was determined before the start of the treatment test, and on day 3, day 5, day 8 (1 week after), day 11, day 15 (after termination of administration, 2 weeks after), day 18, day 21 (3 weeks after), day 25, and day 29 (4 weeks after). A relative tumor volume (RTV) to the tumor volume at the start of the test was obtained for each mouse. Then, the average tumor growth inhibition rate (IR: %) with respect to the control group was calculated on day 15, day 22 (after termination of the treatment period), and day 29 (4 weeks after) in a manner similar to that of Test Example 1. The results are shown in Table 3.

TABLE 3

| Drug | Dose (mg/kg) | X-ray (Gy) | N | IR (%) Day 15 | Day 22 | Day 29 |
|---|---|---|---|---|---|---|
| — | — | 2 | 6 | 21.2 | 16.3 | 25.7 |
| — | — | 5 | 6 | 48.9 | 58.6 | 68.6 |
| TAS-102 | 50 | — | 6 | 22.9 | 32.3 | 48.7 |
| TAS-102 | 50 | 2 | 6 | 48.7 | 55.5 | 60.9 |
| FTD | 50 | — | 6 | 51.8 | 57.2 | 59.0 |
| FTD | 50 | 2 | 6 | 35.8 | 48.6 | 58.5 |

(e) Test Results

Through sole X-ray radiation of 2 Gy, an anti-tumor effect was attained to the LC-11 tumor model on day 15 (21%), on day 22 (16%), and on day 29 (25.7%). When TAS-102 was singly administered, IRs of 23% on day 15, 32% on day 22, and 49% on day 29 were obtained. However, when TAS-102 and radiation were employed in combination, the anti-tumor effect was significantly enhanced, and IRs of 49% on day 15, 55.5% on day 22, and 61% on day 29 were obtained. These values are comparable to those attained through sole X-ray radiation of 5 Gy. Meanwhile, when FTD was singly administered, IRs of 52% on day 15, 57% on day 22, and 59% on day 29 were obtained. However, even when an X-ray radiation of 2 Gy was employed in combination, the anti-tumor effect did not increase. Thus, a TAS-102 pharmaceutical product containing TPI was found to potentiate the anti-tumor effect provided by radiation.

The invention claimed is:

1. A method for treating cancer, consisting essentially of administering, to a subject in need thereof, a uracil derivative represented by formula (1):

[F4]

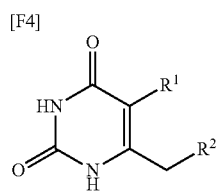

(1)

wherein $R^1$ represents a halogen atom or a cyano group; and $R^2$ represents a 4- to 8-membered heterocyclic group having 1 to 3 nitrogen atoms and optionally having as a substituent a lower alkyl group, an imino group, a hydroxyl group, a hydroxymethyl group, a methanesulfonyloxy group, or an amino group; an amidinothio group in which a hydrogen atom attached to a nitrogen atom optionally substituted by a lower alkyl group; a guanidino group in which a hydrogen atom attached to a nitrogen atom optionally substituted by a lower alkyl group or a cyano group; a lower alkylamidino group; or a 1-pyrrolidinylmethyl group or a pharmaceutically acceptable salt thereof and performing cancer radiation therapy on said subject, in combination with the uracil derivative of formula (1), optionally also in combination with α,α,α-trifluorothymidine.

2. A method according to claim 1, wherein $R^1$ is a chlorine atom, a bromine atom, or a cyano group; and $R^2$ is a 1-pyrrolidinyl group, a 2-iminopyrrolidin-1-yl group, an amidinothio group, a 3-methylguanidino group, or a 1-pyrrolidinylmethyl group.

3. A method according to claim 2, which employs, as an effective ingredient, 5-chloro-6-[1-(2-iminopyrrolidinyl)methyl]uracil or a pharmaceutically acceptable salt thereof.

4. A method according to claim 1, which comprises administering, to said subject, α,α,α-trifluorothymidine in combination with the uracil derivative of formula (1).

5. A method according to claim 2, which comprises administering, to said subject, α,α,α-trifluorothymidine in combination with the uracil derivative of formula (1).

6. A method according to claim 3, which comprises administering, to said subject, α,α,α-trifluorothymidine in combination with the uracil derivative of formula (1).

7. A method according to claim 1, wherein said subject receives a dose of radiation effective to treat cancer in said subject less than a dose when the uracil derivative is not administered to said subject.

* * * * *